(12) United States Patent
Okuda et al.

(10) Patent No.: US 10,810,407 B2
(45) Date of Patent: Oct. 20, 2020

(54) REGION DETECTING METHOD AND REGION DETECTING DEVICE RELATED TO CELL AGGREGATION

(71) Applicants: RIKEN, Saitama (JP); Sumitomo Dainippon Pharma Co., Ltd., Osaka (JP); SUMITOMO CHEMICAL COMPANY, LIMITED, Tokyo (JP)

(72) Inventors: Satoru Okuda, Saitama (JP); Mototsugu Eiraku, Saitama (JP); Atsushi Kuwahara, Kobe (JP)

(73) Assignees: RIKEN, Saitama (JP); Sumitomo Dainippon Pharma Co., Ltd., Osaka (JP); Sumitomo Chemical Company, Limited, Tokyo (JP)

( * ) Notice: Subject to any disclaimer, the term of this patent is extended or adjusted under 35 U.S.C. 154(b) by 142 days.

(21) Appl. No.: 15/778,016

(22) PCT Filed: Nov. 25, 2016

(86) PCT No.: PCT/JP2016/085009
§ 371 (c)(1),
(2) Date: May 22, 2018

(87) PCT Pub. No.: WO2017/090741
PCT Pub. Date: Jun. 1, 2017

(65) Prior Publication Data
US 2018/0349672 A1    Dec. 6, 2018

(30) Foreign Application Priority Data
Nov. 25, 2015   (JP) ................................ 2015-229706

(51) Int. Cl.
*G06K 9/00*         (2006.01)
*G06T 7/12*         (2017.01)
(Continued)

(52) U.S. Cl.
CPC ............. *G06K 9/0014* (2013.01); *C12M 1/34* (2013.01); *C12Q 1/02* (2013.01); *G06K 9/00134* (2013.01);
(Continued)

(58) Field of Classification Search
CPC ...... G06T 7/11; G06T 7/0012; G06K 9/00127
See application file for complete search history.

(56) References Cited

U.S. PATENT DOCUMENTS 10,509,023 B2 * 12/2019 Ichitani .................... G06T 1/00
2005/0002552 A1 *  1/2005 Dunn ................ G01N 15/1475
                                                        382/133
(Continued)

FOREIGN PATENT DOCUMENTS

JP   2010-216920 A    9/2010
WO   2012/117647 A1   9/2012
(Continued)

OTHER PUBLICATIONS

Wang et al. "Segmentation of the Clustered Cells with Optimized Boundary Detection in Negative Phase Contrast Images", PLoS One 10(6): e0130178, Jun. 12, 2015, pp. 1-19 (Year: 2015).*
(Continued)

*Primary Examiner* — Ping Y Hsieh
*Assistant Examiner* — Jose M Torres
(74) *Attorney, Agent, or Firm* — Morgan, Lewis & Bockius LLP (57) ABSTRACT

A specific region such as a continuous epithelial structure is automatically detected in a cell aggregate. A region detecting method includes an input step (S01) of inputting an image obtained by imaging a cell aggregate, an outline detecting step (S02) of detecting an outline of the cell aggregate together with an order along the outline from the input image, a region detecting step (S03) of detecting a
(Continued)

specific region included in the cell aggregate based on the detected outline and order, and an output step (S04) of outputting information indicating the detected region.

7 Claims, 9 Drawing Sheets

(51) Int. Cl.
  *G06T 7/181* (2017.01)
  *C12M 1/34* (2006.01)
  *C12Q 1/02* (2006.01)
  *G06T 7/33* (2017.01)
  *G02B 21/36* (2006.01)
(52) U.S. Cl.
  CPC ............... *G06T 7/12* (2017.01); *G06T 7/181* (2017.01); *G06T 7/337* (2017.01); *G02B 21/365* (2013.01); *G06T 2207/10056* (2013.01); *G06T 2207/10064* (2013.01); *G06T 2207/30024* (2013.01)

(56) References Cited

U.S. PATENT DOCUMENTS

| | | | |
|---|---|---|---|
| 2006/0013455 A1* | 1/2006 | Watson | G06K 9/0014 382/128 |
| 2006/0083418 A1* | 4/2006 | Watson | G06T 7/62 382/133 |
| 2012/0114219 A1* | 5/2012 | Nakagawa | C12M 41/14 382/133 |
| 2012/0237109 A1* | 9/2012 | Rajpoot | G06T 7/0012 382/134 |
| 2015/0010218 A1* | 1/2015 | Bayer | G06K 9/0014 382/128 |
| 2015/0169985 A1* | 6/2015 | Burger | G06T 7/11 382/133 |
| 2016/0364599 A1* | 12/2016 | Tsujimoto | G02B 21/14 |
| 2017/0370901 A1* | 12/2017 | Ichitani | G01N 33/48 |

FOREIGN PATENT DOCUMENTS

| | | |
|---|---|---|
| WO | 2015/025967 A1 | 2/2015 |
| WO | 2015/141275 A1 | 9/2015 |

OTHER PUBLICATIONS

Nakano et al., "Self-Formation of Optic Cups and Storage Stratified Neural Retina from Human ESCs," Cell Stem Cell, 10: 771-785 (2012).

Teh et al., "On the Detection of Dominant Points on Digital Curves," IEEE Transactions on Pattern Analysis and Machine Intelligence, 11: 859-872 (1989).

Nakagawa et al., "A novel efficient feeder-free culture system for the derivation of human induced pluripotent stem cells," Scientific Reports, 4: 3594 (2014).

Kuwahara et al., "Generation of a ciliary margin-like stem cell niche from self-organizing human retinal tissue," Nature Communications, 6: 6286, 1-15 (2015).

International Search Report issued in corresponding International Patent Application No. PCT/JP2016/085009 dated Feb. 21, 2017.

International Preliminary Report on Patentability and Written Opinion issued in corresponding International Patent Application No. PCT/JP2016/085009 dated Jun. 7, 2018.

* cited by examiner

REGION DETECTING METHOD AND REGION DETECTING DEVICE RELATED TO CELL AGGREGATION

CROSS-REFERENCE TO RELATED APPLICATION

Priority is claimed on Japanese Patent Application No. 2015-229706, filed Nov. 25, 2015, the content of which is incorporated herein by reference.

TECHNICAL FIELD

The present invention relates to a region detecting method and a region detecting device through which a specific region included in a cell aggregate is detected in an image obtained by imaging the cell aggregate.

BACKGROUND ART

Epithelial tissue (for example, retinal tissue) of an animal has a characteristic structure called a continuous epithelial structure. In recent years, methods of forming a cell aggregate from pluripotent stem cells and producing three-dimensional tissues in a test tube have been developed (for example, refer to Patent Literature 1 and Non-Patent Literature 1). A cell aggregate has various morphological characteristics, and a part thereof may include a continuous epithelial structure. Within a cell aggregate, a continuous epithelial structure is a region containing cells that have particularly high quality and are useful. As a technique of separating a continuous epithelial structure from a cell aggregate and refining it, a method in which a skilled researcher visually detects a continuous epithelial structure using a microscope or the like and separates and refines it is known (for example, refer to Patent Literature 1 and Non-Patent Literature 1 and 2).

CITATION LIST

Patent Literature

[Patent Literature 1] WO 2015/025967

Non-Patent Literature

[Non-Patent Literature 1] Nature Communications, 6, 6286 (2015)
[Non-Patent Literature 2] Cell Stem Cell, 10(6), 771-775 (2012)

SUMMARY OF INVENTION

Technical Problem

However, there is a problem in that time and effort are required for visually detecting a continuous epithelial structure in a large number of cell aggregates. Thus, a method of automatically detecting a continuous epithelial structure in a cell aggregate is desired.

The present invention has been made in view of the above circumstances, and an object of the present invention is to provide a region detecting method and a region detecting device through which it is possible to automatically detect a specific region such as a continuous epithelial structure in a cell aggregate.

Solution to Problem

In order to achieve the above object, a region detecting method according to an embodiment of the present invention is a method of operating a region detecting device. The region detecting method includes an input step of inputting an image obtained by imaging a cell aggregate; an outline detecting step of detecting an outline of the cell aggregate together with an order along the outline in the image input in the input step; a region detecting step of detecting a specific region included in the cell aggregate based on the outline and order detected in the outline detecting step; and an output step of outputting information indicating the region detected in the region detecting step.

In the region detecting method according to an embodiment of the present invention, a specific region is detected based on the outline and order of the cell aggregate detected in the image. Therefore, in the region detecting method according to an embodiment of the present invention, it is possible to automatically detect a specific region such as a continuous epithelial structure along an outline of a cell aggregate.

In the outline detecting step, outline tracking processing may be performed on the image, thereby detecting the outline of the cell aggregate. In addition, in the outline detecting step, smoothing processing may be performed on the image before the outline tracking processing. According to this configuration, it is possible to reliably and suitably detect the outline and order of the cell aggregate.

In the region detecting step, a specific region may be detected based on luminance values of pixels in a direction from the outline to the cell aggregate in the image. In addition, in the region detecting step, a specific region may be detected based on a shape of the outline in the image. More specifically, in the region detecting step, a shape of the outline in the image may be expressed as a curvature of pixels constituting the outline in an outline tangential direction and the specific region may be detected based on the curvature. According to this configuration, it is possible to suitably detect a specific region.

In addition, the specific region may be a region of the continuous epithelial structure. According to this configuration, it is possible to automatically detect a region of the continuous epithelial structure.

In addition, the cell aggregate may include retinal tissue. According to this configuration, it is possible to automatically detect a specific region in the cell aggregate including retinal tissue.

Incidentally, the present invention can be described as an invention of a region detecting device to be described below in addition to the invention of the region detecting method as described above. These inventions are substantially the same invention, differing merely in category and have the same operations and effects.

That is, a region detecting device according to an embodiment of the present invention includes input means configured to input an image obtained by imaging a cell aggregate; outline detection means configured to detect an outline of the cell aggregate together with an order along the outline in the image input by the input means; region detection means configured to detect a specific region included in the cell aggregate based on the outline and order detected by the outline detection means; and output means configured to output information indicating the region detected by the region detection means.

That is, an embodiment of the present invention is as follows.

[1] A region detecting method which is a method of operating a region detecting device, the method including
an input step of inputting an image obtained by imaging a cell aggregate;
an outline detecting step of detecting an outline of the cell aggregate together with an order along the outline in the image input in the input step;
a region detecting step of detecting a specific region included in the cell aggregate based on the outline and order detected in the outline detecting step; and
an output step of outputting information indicating the region detected in the region detecting step.

[2] The region detecting method according to [1],
wherein, in the outline detecting step, outline tracking processing is performed on the image, thereby detecting the outline of the cell aggregate.

[3] The region detecting method according to [2],
wherein, in the outline detecting step, smoothing processing is performed on the image before the outline tracking processing.

[4] The region detecting method according to any one of [1] to [3],
wherein, in the region detecting step, the specific region is detected based on luminance values of pixels in a direction from the outline to the cell aggregate in the image.

[5] The region detecting method according to any one of [1] to [4],
wherein, in the region detecting step, the specific region is detected based on a shape of the outline in the image.

[6] The region detecting method according to [5],
wherein, in the region detecting step, a shape of the outline in the image is expressed as a curvature of pixels constituting the outline in an outline tangential direction and the specific region is detected based on the curvature.

[7] The region detecting method according to any one of [1] to [6],
wherein the specific region is a region of a continuous epithelial structure.

[8] The region detecting method according to any one of [1] to [7], wherein the cell aggregate includes retinal tissue.

[9] A region detecting device including:
input means configured to input an image obtained by imaging a cell aggregate;
outline detection means configured to detect an outline of the cell aggregate together with an order along the outline in the image input by the input means;
region detection means configured to detect a specific region included in the cell aggregate based on the outline and order detected by the outline detection means; and
output means configured to output information indicating the region detected by the region detection means.

Advantageous Effects of Invention

In an embodiment of the present invention, a specific region is detected based on an outline and order of a cell aggregate detected in an image. Therefore, according to an embodiment of the present invention, it is possible to automatically detect a specific region such as a continuous epithelial structure along an outline of a cell aggregate.

DESCRIPTION OF EMBODIMENTS

A region detecting device and a region detecting method according to embodiments of the present invention will be described below in detail with reference to the drawings. Hereinafter, in the description of the drawings, the same components will be denoted with the same reference numerals and redundant description thereof will be omitted.

Figure 1:
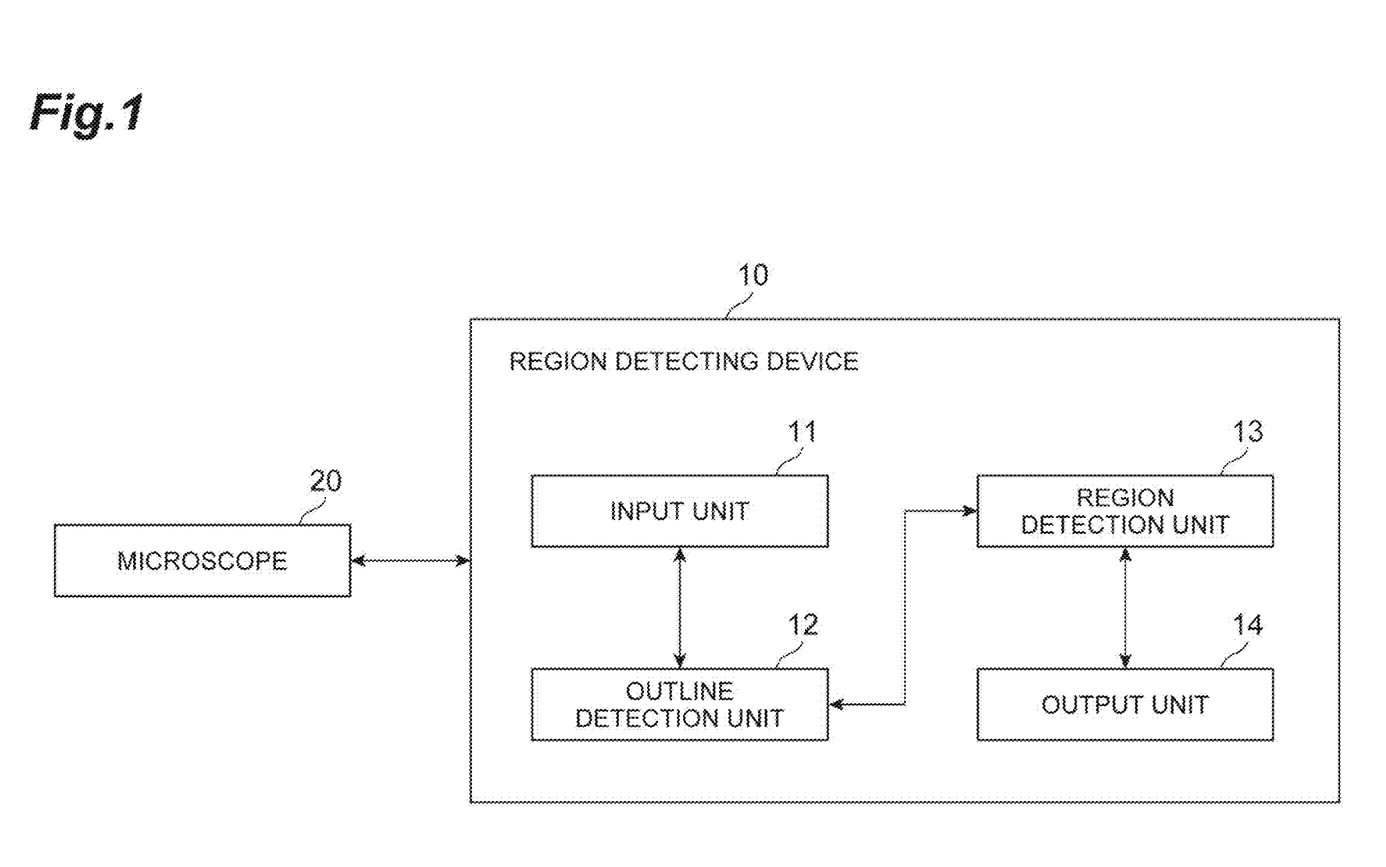
FIG. 1 is a diagram showing a configuration of a region detecting device according to an embodiment of the present invention.

FIG. 1 shows a region detecting device 10 according to the present embodiment. The region detecting device 10 is a device configured to input an image obtained by imaging (photographing) a cell aggregate and detect a specific region included in the cell aggregate in the image. Specifically, the region detecting device 10 may be a computer including hardware such as a central processing unit (CPU), a memory, and a communication module.

For example, as described above, the region detecting device 10 may detect a region of tissue having specific morphological characteristics (morphological features) as a specific region in an image obtained by imaging a cell aggregate formed of pluripotent stein cells. Specifically, a region of a continuous epithelial structure may be detected in a cell aggregate including retinal tissue. According to detection performed by the region detecting device 10, it is possible to determine a cell aggregate including a continuous epithelial structure and the continuous epithelial structure in the cell aggregate without performing staining of the cell aggregate or the like, and it is possible to easily separate the continuous epithelial structure from the cell aggregate and refine it.

In an embodiment of the present invention, cells include epithelial cells and mesenchymal cells according to a morphological classification of cells in developmental biology. Epithelial cells have polarity in the apical-basal axis. The apical side is usually a space side. On the other hand, the basal side has a basement membrane and is in contact with an extra-cellular matrix. Regarding epithelial cells, epithelial cells are firmly adhered to each other according to adherence junctions or tight junctions on the apical side and can form epithelial tissue (epithelium). Epithelial tissue is also referred to as an epithelial sheet, and includes a simple squamous epithelium, a simple columnar epithelium, and a stratified squamous epithelium. Mesenchymal cells are cells that have weak apical-basal polarity, and weak contribution to adherence junctions and tight junctions, and are unlikely to form a sheet. Mesenchymal cells are frequently scattered in the form of star in an extra-cellular matrix in vivo.

In an embodiment of the present invention, a cell aggregate is a mass formed of aggregated cells and is a mass in which cells are adhered to each other. Aggregates of cells, embryoid bodies, spheres, and spheroids are also included in a cell aggregate. In addition, a "cell aggregate" in this specification is not necessarily formed of a plurality of cells, and it may be formed of one cell. That is, a cell aggregate in this specification includes a "cell aggregate formed of a plurality of cells" and a "single cell." In an embodiment of the present invention, examples of a cell aggregate include a cell aggregate that can be cultured in vitro, a tissue piece cut out from a living body, a cell aggregate in a suspension culture, a cell aggregate in an adhesion culture, a frozen cell aggregate, and a single cell. In addition, in an embodiment of the present invention, a cell aggregate may be particularly a cell aggregate that can be cultured in vitro, a cell aggregate in a suspension culture, or a cell aggregate in an adhesion culture. In an embodiment of the present invention, a cell aggregate includes either or both of proliferating cells and non-proliferating cells (growth-arrested cells). In an embodiment of the present invention, a cell aggregate includes either or both of epithelial cells and mesenchymal cells. When either or both of epithelial cells and mesenchymal cells are gathered in a cell aggregate, the cells are adhered to each other and form a tissue. The tissue has morphological characteristics. The morphological characteristics are regulated (determined) by the type of cells, the orientation of cells, biological properties of cells, physical properties of cells, dynamic properties of cells, characteristics of an extracellular matrix that the tissue possesses, and the like. Examples of tissues of a cell aggregate having specific morphological characteristics include epithelial tissue, mesenchymal tissue, rosettes, luminal structures and continuous epithelial tissue, and the like.

In an embodiment of the present invention, a continuous epithelial structure refers to a state in which there is a continuous epithelial tissue. When it is described that there is a continuous epithelial tissue, this refers to a state in which, for example, 10 cells to 10,000,000 cells are arranged in a tangential direction. In addition, when it is described that there is a continuous epithelial tissue, this may particularly refer to a state in which 30 cells to 10,000,000 cells are arranged in a tangential direction. Furthermore, when it is described that there is a continuous epithelial tissue, this may particularly refer to a state in which 100 cells to 10,000,000 cells are arranged in a tangential direction. Whether there are continuous epithelial cells or not can be determined by immunostaining with atypical-PKC, E-cadherin, and N-cadherin which are apical markers or staining of a cell nucleus (for example, DAPI staining, PI staining, Hoechst staining, or staining with marker proteins (such as Rx, Chx10, Ki67, and Crx) localized in a cell nucleus or the like). As a continuous epithelial structure, an epithelial tissue in a living animal body, for example, a neuroepithelial structure, an epidermal epithelial structure, an intestinal epithelial structure, and a hepatocyte epithelial structure may be exemplified. Cells that are cultured outside an animal body can also form a continuous epithelial structure. Examples of a cell aggregate including a continuous epithelial structure that can be cultured outside an animal body include neural tissue, epidermal tissue, intestinal epithelial tissue, and liver tissue. Examples of neural tissue include retinal tissue (including a three-dimensional retina). Retinal tissue can be prepared by a known method (for example, methods described in Non-Patent Literature 1 and 2).

In an embodiment of the present invention, the tangential direction with respect to the epithelial tissue refers to a direction in which cells are arranged when each cell in the epithelial tissue is arranged in a certain direction and is a parallel direction or a lateral direction with respect to the epithelial tissue (or epithelial sheet). In an embodiment of the present invention, a perpendicular direction with respect to the epithelial tissue refers to a direction perpendicular to a direction in which cells are arranged when each cell in the epithelial tissue is arranged in a certain direction and is a perpendicular direction or a longitudinal direction with respect to the epithelial tissue (or epithelial sheet).

In an embodiment of the present invention, "retinal tissue" refers to a tissue in which one type or at least a plurality of types of cells such as photoreceptors, photoreceptor precursor cells, rod photoreceptors, cone photoreceptors, interneurons, horizontal cells, bipolar cells, amacrine cells, retinal ganglion cells (ganglion cells), retinal pigment epithelial cells (RPE), ciliary marginal zone cells, progenitor cells thereof, or retinal progenitor cells, which constitute retinal layers in a retina in vivo, are three-dimensionally arranged in layers. Whether each cell constitutes which retinal layer is formed can be confirmed by a known method, for example, using expression of a cell marker or a degree thereof.

A continuous epithelial structure included in a cell aggregate has the following morphological features in a bright-field image.

Feature 1: A part (surface layer) close to the outer circumference of the cell aggregate has a high luminance value (intensity) (is bright), and an inside part (a deep layer in the cells) with a certain depth from a surface layer of the cell aggregate has a small luminance value Feature 2: the outline of the cell aggregate is smooth (that is, an amount of variation in curvature is low).

Feature 3: The morphological features of Feature 1 and Feature 2 are continuous in the tangential direction of aggregates These features were found by the inventors and are the basis of the present invention.

Subsequently, functions of the region detecting device 10 according to the present embodiment will be described. As shown in FIG. 1, the region detecting device 10 includes an input unit 11, an outline detection unit 12, a region detection unit 13, and an output unit 14.

The input unit 11 is input means configured to input an image obtained by imaging a cell aggregate. As the image obtained by imaging a cell aggregate, for example, a bright-field image, a dark-field image, a phase contrast image, a Hoffman modulation contrast image, or a differential interference image can be used, but the image is not particularly limited. In addition, as the image, particularly, a phase contrast image, a Hoffman modulation contrast image or a differential interference image may be used. Further, as the image, particularly a phase contrast image may be used. As the image, for example, a fluorescence image can be used other than the above images. As the image, an image in which at least a part of an outline of a cell aggregate is shown is used. In addition, particularly, an image in which the entire outline of a cell aggregate is shown may be used. In addition, particularly, a background color of an image may be a color that can be clearly distinguished from the cell aggregate.

As an imaging device configured to capture (acquire) an image, a microscope can be used. For example, an optical microscope, an inverted microscope, an upright microscope, a fluorescence microscope, a confocal microscope, a spinning disk confocal microscope, a stereomicroscope, or a zoom microscope can be used. As a device configured to capture an image of a cell aggregate with a size of about 0.3 mm to 3 mm, particularly, an inverted microscope or a stereomicroscope may be used. For example, when a phase contrast image is used, a phase contrast microscope is used. When a differential interference image is used, a differential interference microscope is used. When a Hoffman modulation contrast image is used, an inverted microscope or an upright microscope is used. When a fluorescence image is used, a fluorescence microscope is used. In addition, an imaging device other than a microscope, for example, a camera, may be used. Images input to the input unit 11 are, for example, images shown in FIGS. 2(a) to 2(c) and FIG. 3 to FIG. 8(a).

For example, the region detecting device 10 may be connected to a microscope 20 as shown in FIG. 1 so that it transmits and receives information. The input unit 11 receives an image captured and obtained by the microscope 20 from the microscope 20 and inputs the image. In addition, the input unit 11 may input an image by any method other than the above method, for example, by reading an image that is stored in advance in the region detecting device 10 by operation of a user of the region detecting device 10. The input unit 11 outputs the input image to the outline detection unit 12.

The outline detection unit 12 is outline detection means configured to detect (extract) an outline of a cell aggregate in the image input by the input unit 11 together with an order along the outline, that is, perform outline extraction processing. Here, the outline in an embodiment of the present invention refers to a boundary between a background region and a cell aggregate. The order along the outline may be any order by which position coordinates of pixels indicating an outline of a cell aggregate can be distinguished in clockwise or counterclockwise order using a specific pixel showing an outline of the cell aggregate as a starting point.

The outline detection unit 12 performs, for example, outline tracking processing on an image, thereby detecting the outline of the cell aggregate. In addition, the outline detection unit 12 may particularly perform at least any of binarization processing and smoothing processing on the image before the outline tracking processing. In addition, the outline detection unit 12 may perform processing on the image particularly in the order of binarization processing, smoothing processing, and outline tracking processing. For a process used for outline extraction processing, a known method, for example, a method described in Computer Image Processing, Hideyuki Tamura, Ohmsha, 2002, can be used.

The binarization processing is processing in which a luminance value (pixel value, color tone) of each pixel included in an image is replaced with any of two defined values. The two defined values may be two arbitrary values, for example, a combination of a luminance value of 0 and a luminance value of 255 and a combination of a luminance value of 10 and a luminance value of 100, but the values are not particularly limited. For the binarization processing, for example, a technique in which a common threshold value is used for the entire image, a technique in which a different threshold value is used for each local part of an image, and the like may be used without particular limitation. For example, there is a technique in which, when two defined values are a combination of a luminance value of 0 and a luminance value of 255, if a luminance value of each pixel is higher than a threshold value, the value is replaced with a luminance value of 255 (light), and if a luminance value of each pixel is lower than a threshold value, the value is replaced with a luminance value of 0 (dark). When binarization processing is performed, it is possible to easily distinguish a part in which a cell aggregate is exhibited and a background part in the image. For example, in the above case, a pixel part (dark region) with a luminance value of 0 may be regarded as a part (cell aggregate region) in which a cell aggregate is shown and a pixel part (light region) with a luminance value of 255 may be regarded as a background part (background region).

The smoothing processing is processing in which a spatial distribution of luminance values of an image is smoothed. Examples of the smoothing processing include moving average filtering, Gaussian filtering, expansion and reduction processing, and combination thereof, but the smoothing processing is not particularly limited. In addition, as the smoothing processing, particularly, expansion and reduction processing may be used. When the smoothing processing is performed, at least any effect of an effect of reducing outlying parts (for example, pixels positioned outside an outline of a cell aggregate) and an effect of making a thickness of an outline of a cell aggregate be a certain thickness or more is obtained, and the outline (that is, a boundary between the dark region and the light region) of a cell aggregate can become clearer.

Here, when the outline tracking processing is performed without performing the smoothing processing, it may not possible to determine the order (arrangement) of pixels which is an order of an outline of a cell aggregate depending on an image, and the outline extraction processing may not be performed properly. When the smoothing processing is performed, it is possible to determine the order of pixels in an arbitrary image.

The outline tracking processing (or chain approximation processing, chain type approximation processing) is processing through which an outline (a boundary between a dark region and a light region when binarization processing is performed) of a cell aggregate included in an image is detected and position coordinates of pixels constituting the outline are sequentially arranged along the outline. Examples of an outline tracking processing method include a method proposed by Teh and Chin (Teh, C. H. and Chin, R. T., On the Detection of Dominant Points on Digital Curves, PAMI 11 8, pp 859-872, 1989) but the method is not particularly limited. Examples of the outline tracking processing method include a method including an outline tracking calculating step. In calculation of the outline tracking calculating step, luminance values of adjacent surrounding pixels centered on a selected pixel (called a center pixel) are sequentially arranged in a certain direction (for example, a clockwise direction or a counterclockwise direction), a pixel (adjacent outline pixel) immediately before a luminance value decreases with respect to the forward direction in the row is extracted and a position of the extracted pixel is designated as a new center pixel.

For example, the outline detection unit 12 may select one pixel (for example, a pixel with the smallest X and Y coordinates among pixels in a dark region,) in the dark region (pixels with a luminance value of 0) adjacent to a light region (pixels with a luminance value of 255) and perform the above outline tracking calculating step using the pixel as a processing starting point (that is, an initial position which is the first center point, indicated as "0" in FIG. 3 to FIG. 8(a)) for an outline of the cell aggregate. The outline detection unit 12 consecutively performs the outline tracking calculating step a plurality of times until the position of the extracted adjacent outline pixel matches the position (initial position) of the processing starting point. The outline detection unit 12 sets a set of the center pixels obtained in this manner as pixels indicating the outline of the cell aggregate.

The outline detection unit 12 outputs the outline information indicating the outline of the cell aggregate obtained in the above processing to the region detection unit 13 together with the image. In an embodiment of the present invention, the outline information is information including "information about a set of position coordinates of pixels indicating the outline" and "an order (arrangement) of the pixels." According to the outline information, the order of position coordinates of pixels indicating the outline along the outline can be distinguished. As the outline information, particularly, information (a list) in which position coordinates of pixels indicating the outline are arranged in order along the outline may be used.

The region detection unit 13 is region detection means configured to detect (extract) a specific region included in a cell aggregate based on the outline and order detected by the outline detection unit 12. For example, the region detection unit 13 may detect a specific region based on luminance values of pixels in a direction from the outline to the cell aggregate in the image or detects a specific region based on the shape of the outline in the image, but the present invention is not limited thereto. For example, the shape of the outline in the image may be expressed as a curvature of each pixel constituting the outline in an outline tangential direction, and the region detection unit 13 may detect a specific region based on the curvature as detection based on the shape of the outline. A region to be detected is set in advance. For example, the region to be detected may be the continuous epithelial structure region described above. In some aspects, specifically, the region detection unit 13 detects a specific region as follows.

In the following, the outline tangential direction is a direction parallel to the outline at an arbitrary point on the outline of the cell aggregate included in the image. The outline perpendicular direction is a direction perpendicular to the outline at an arbitrary point on the outline of the cell aggregate included in the image (not a direction from the outline to outside of the cell aggregate, but a direction from the outline to the cell aggregate). Examples of the direction from the outline to a cell aggregate include a direction from 30 degrees to 150 degrees with respect to the outline. In addition, the direction may be particularly a direction from 60 degrees to 120 degrees with respect to the outline. Furthermore, the direction may be particularly a direction of 90 degrees with respect to the outline (a direction perpendicular to the outline).

The region detection unit 13 computes a curvature (outline curvature distribution) of each pixel constituting the outline in the outline tangential direction as values indicating the shape of the outline based on outline information input from the outline detection unit 12. The region detection unit 13 determines two pixels that are in front of and behind a pixel for which a curvature is to be computed by a preset distance in the order of the outline (for example, the number of preset pixels; particularly, a distance along the outline). The region detection unit 13 computes a circle that crosses position coordinates of the pixel for which a curvature is to be computed and position coordinates of the two determined pixels. The region detection unit 13 sets a reciprocal number of the radius of the circle as the curvature. When the center of the circle that crosses three points with respect to a pixel for which a curvature is to be computed is on the inside of (inside the outline) of the cell aggregate (aggregate of cells), the curvature can be positive. When the center of the circle that crosses three points with respect to a pixel for which a curvature is to be computed is on the outside (outside the outline) of the cell aggregate (aggregate of cells), the curvature can be negative. When a total of three pixels including a pixel for which a curvature is to be computed and two pixels that are separately selected are positioned on a straight line, any value (for example, 0) may be appropriately used as the curvature. Here, the method of computing a curvature is not limited to the above method, and the curvature may be computed by any method. FIG. 3 to FIG. 6(c), FIG. 7, and FIG. 8(b) show graphs of examples of curvatures computed for pixels constituting an outline. In the graphs, the abscissa axis (x axis) represents the position of the pixel along the outline (the position of the pixel if the outline is a straight line). The direction in this case is clockwise. The ordinate axis (y axis) represents the value of the curvature.

On the other hand, the region detection unit 13 determines luminance values of pixels (before binarization) in the outline perpendicular direction for pixels constituting the outline. In this case, the region detection unit 13 determines an outline perpendicular direction from pixels based on the order of pixels of the outline. For example, two pixels that are in front of and behind a pixel for which an outline perpendicular direction is to be computed by a preset distance (for example, the number of preset pixels; particularly, a distance along the outline) in the order of the outline are determined. The region detection unit 13 computes a circle that crosses position coordinates of the pixel for which an outline perpendicular direction is to be computed and two determined pixels. The region detection unit 13 sets a direction toward the inside of the aggregate in a straight line that crosses the pixel for which an outline perpendicular direction and the center of the circle as the outline perpendicular direction. FIG. 3 to FIG. 6(b) show examples of luminance values of the pixels in the determined outline perpendicular direction. In FIG. 3 to FIG. 6(b), the abscissa axis (x axis) represents positions of pixels along the outline and the ordinate axis (z direction, depth direction) represents the luminance value of pixels in the depth direction from pixels constituting the outline.

Next, the region detection unit 13 computes an average value (luminance value distribution) of luminance values in a preset range (region) in the outline perpendicular direction from luminance values of determined pixels with respect to each pixel constituting the outline. A plurality of ranges may be provided for each depth (distance) from the position of the outline. For example, five ranges may be set for each depth and an average value of luminance values is computed for each of the ranges. FIG. 3 to FIG. 6(d), FIG. 7, and FIG. 8(c) show graphs of examples of the average value of luminance values computed with respect to each pixel constituting the outline. In the graphs, the abscissa axis (x axis) represents the position of the pixel along the outline and the ordinate axis (z direction, depth direction) represents the average luminance value of luminance values. In the graphs, the value indicated by "1/5" is an average luminance value in the range with the shallowest depth from the outline and "2/5," "3/5," "4/5," and "5/5" in order are average luminance values in deeper ranges.

As described above, the curvature and the average luminance value are values that cannot be computed without using the order of pixels along the outline. The region detection unit 13 detects a specific region based on the curvature and average luminance value computed as described above. A continuous epithelial structure is a tissue that is positioned on the outline part of the cell aggregate. Here, when a region of a continuous epithelial structure is detected, the region detection unit 13 detects which part of the outline corresponds to the continuous epithelial structure. The region detection unit 13 has conditions for detecting a region of a continuous epithelial structure already stored therein and detects the region based on these criteria.

For example, the region detection unit 13 may determine whether the following conditions are satisfied at each point (position coordinates of a pixel of an outline) on the outline. (Condition 1) An absolute value C of a curvature is smaller than a preset threshold value C1 (for example, C1 is 0.10) (Condition 2) An average luminance value on "⅕" and "⅖" is greater than a preset threshold value (for example, 700) (Condition 3) An average luminance value on "⅗" and "5/5" is smaller than a preset threshold value (for example, 500) (Condition 4) A range (a length of an outline: L) that includes the point and consecutively satisfies the above conditions 1 to 3 is equal to or greater than a preset length (for example, 350).

The region detection unit 13 determines that there is a continuous epithelial structure at a position of a point at which the above conditions 1 to 4 are satisfied. For example, in the example in FIG. 3, in the image in FIG. 3*a*, a region between 0 and a, a region between b and c, and a region between c and 0 are determined as regions in which there is a continuous epithelial structure. Here, the above threshold value may be appropriately set according to conditions in which an image is captured, detection conditions, and the like. In addition, the above conditions themselves may be appropriately set according to a tissue related to a region to be detected and the like.

The region detection unit 13 outputs information indicating the detected region to the output unit 14. The information is, for example, information indicating coordinates of the region on the image.

The output unit 14 is output means configured to output information indicating a region detected by the region detection unit 13. For example, the output unit 14 may display information indicating the region. When the information is displayed, information indicating the region may be displayed on the image to be detected in an overlapping manner so that it is easy to recognize which part is the detected region. It is possible to easily separate a continuous epithelial structure from a cell aggregate and refine it with reference to the output. In addition, the output of information is not limited to display. For example, information may be transmitted to another device. Functions of the region detecting device 10 according to the present embodiment are described above.

Figure 9:
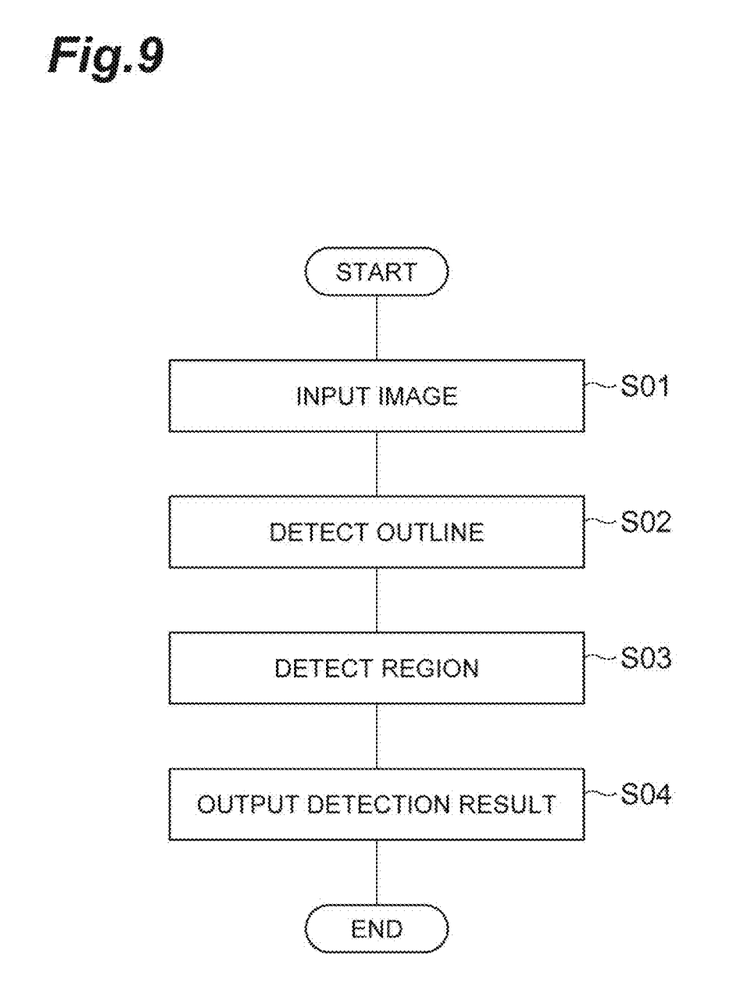
FIG. 9 is a flowchart showing processes (detecting region method) performed by a region detecting device according to an embodiment of the present invention.

Subsequently, a region detecting method which is a process (a method of operating the region detecting device 10) performed by the region detecting device 10 according to the present embodiment will be described with reference to a flowchart in FIG. 9. In this process, first, an image obtained by imaging a cell aggregate is input by the input unit 11 (S01, input step). Next, the outline detection unit 12 detects an outline of the cell aggregate together with an order along the outline in the image (S02, outline detecting step). Next, the region detection unit 13 detects a specific region included in the cell aggregate based on the detected outline and order (S03, region detecting step). Next, the output unit 14 outputs information indicating the detected region (S04, output step). The processes performed by the region detecting device 10 according to the present embodiment are described above.

As described above, in the present embodiment, a specific region is detected based on the outline of the cell aggregate and the order detected in the image. The continuous epithelial structure exemplified as a detection target in the present embodiment is present along the outline of the cell aggregate. Thus, the outline of the cell aggregate in the image corresponds to the presence of a continuous epithelial structure. Here, when the order of the outline is used as in the present embodiment, for example, a curvature of the outline and luminance values of pixels in the outline perpendicular direction are computed, and thus the result can be used for detecting a specific region. Thereby, it is possible to detect a specific region precisely. Therefore, according to the present embodiment, it is possible to automatically detect a specific region such as a continuous epithelial structure along the outline of a cell aggregate and the like.

In addition, as in the present embodiment, the outline may be detected by outline tracking processing. Furthermore, at least any of binarization processing and smoothing processing may be performed before the outline tracking processing. In this case, particularly, processing may be performed "in the order of binarization processing, smoothing processing, and outline tracking processing" or "in the order of smoothing processing, binarization processing, and outline tracking processing." In addition, particularly, processing may be performed in the order of binarization processing, smoothing processing, and outline tracking processing. According to these configurations, it is possible to reliably and suitably detect the outline of the cell aggregate and the order. However, the outline may be detected by any method as long as the order of the outline can be detected by the method.

In addition, as in the present embodiment, a specific region may be detected using luminance values of pixels in the outline perpendicular direction. In addition, in the luminance values of pixels, a change in the outline perpendicular direction may be computed and used for detecting a specific region. In addition, a specific region may be detected using a shape of the outline such as the curvature of the outline. According to these configurations, it is possible to suitably detect a specific region.

Here, while an example in which a region of a continuous epithelial structure is detected in the cell aggregate including retinal tissue has been described in the present embodiment, a cell aggregate as a region detection source is not limited to a cell aggregate including retinal tissue. In addition, the specific region to be detected is not limited to a continuous epithelial structure, and may be any region as long as it influences the outline of the cell aggregate in the image. In addition, when the cell aggregate is one cell, examples of the specific region to be detected include a leading edge, a growth cone, adherence junctions, and tight junctions, but the region is not particularly limited.

EXAMPLES

An embodiment of the present invention will be described below in detail with reference to examples. However, the present invention is not limited to such examples.

Example 1

In the present example, the generation of a cell aggregate itself which is a region to be detected is also described. Human IPS cells (1231A3 cell line, available from Kyoto University) were cultured in feeder-free conditions according to the method described in "Scientific Reports, 4, 3594(2014)." A StemFit medium (AK03 commercially available from Ajinomoto Co., Inc.) was used as a feeder-free medium and Laminin 511-E8 (commercially available from Nippi. Inc.) was used as a feeder-free scaffold.

As a specific maintenance culture operation, first, human iPS cells (1231A3 cell line) that became subconfluent were washed with PBS, and were then dispersed in single cells using TrypLE Select (commercially available from Life Technologies). Then, the human iPS cells dispersed in the single cells were seeded on a plastic culture dish coated with Laminin 511-E8, and cultured in feeder-free conditions in a StemFit medium in the presence of Y27632 (10 µM). When a 6-well plate (commercially available from IWAKI & Co., Ltd., for cell culture, culture area of 9.4 cm$^2$) was used as the plastic culture dish, the number of seed cells of human iPS cells dispersed in single cells was 6×10$^3$. One day after seeding, the medium was replaced with a StemFit medium containing no Y27632. Thereafter, the medium was replaced with a StemFit medium containing no Y27632 once every 1 day or 2 days. Then, 6 days after seeding, the cells were cultured until they became subconfluent (to an extent that 60% of the culture area was covered with cells).

As a differentiation induction operation, human iPS cells (1231A3 cell line) were cultured in feeder-free conditions using a StemFit medium until one day before subconfluence. Human iPS cells one day before the subconfluence were cultured in feeder-free conditions for 1 day in the presence of SB431542 (5 µM) and SAG (300 nM) (precondition process).

The human iPS cells that were subjected to the precondition process were treated with a cell dispersion solution using TrypLE Select (commercially available from Life Technologies) and additionally dispersed in single cells according to a pipetting operation. Then, the human iPS cells dispersed in the single cells were suspended in 100 µl of a serum-free medium so that 1.2×10$^4$ cells were contained in each well of a non-cell-adhesive 96-well culture plate (PrimeSurface 96V bottom plate commercially available from Sumitomo Bakelite Co., Ltd.) and suspended and cultured at 37° C. with 5% CO$_2$. As the serum-free medium (gfCDM+KSR) in this case, a serum-free medium in which 10% KSR, 450 µM 1-monothioglycerol, and 1×chemically defined lipid concentrate were added to a mixed solution containing an F-12 medium and an IMDM medium (1:1) was used. When the suspension culture started (day 0 after the suspension culture started), Y27632 (final concentration of 20 µM) and SAG (final concentration of 30 nM) were added to the serum-free medium. 3 days after the suspension culture started, in a medium containing neither of Y27632 and SAG, but containing recombinant human BMP4 (commercially available from R&D), 50 µl of the fresh serum-free medium described above was added so that a final concentration of exogenous recombinant human BMP4 was 1.5 nM (55 ng/ml). Then, half of the volume of the above serum-free medium containing neither of Y27632 and recombinant human BMP4 was replaced once every 2 or 4 days. As a half volume medium exchange operation, half of the volume of the medium in a culture container, that is, 75 µl, was discarded, and 75 µl of fresh serum-free medium described above was added, where the total volume of the medium was 150 µl.

Aggregates of cells from 17 days after the suspension culture started obtained in this manner were cultured for 3 days, that is, 20 days after the suspension culture started in a serum-free medium containing CHIR99021 (3 µM) and SU5402 (5 µM) (a medium in which a 1% N2 supplement was added to a DMEM/F12 medium).

In addition, Aggregates of cells from 20 days after the suspension culture started were suspended and cultured in a serum medium containing neither of a Wnt signaling pathway active substance and an FGF signaling pathway inhibitor (a medium in which 10% fetal bovine serum, 1% N2 supplement, 0.5 µM retinoic acid, and 100 µM taurine were added to a DMEM/F12 medium) for 43 days, that is, 63 days after the suspension culture started. About half of the volume of the serum medium was replaced once every 2 or 4 days from 20 days to 63 days after the suspension culture started.

Figure 2:
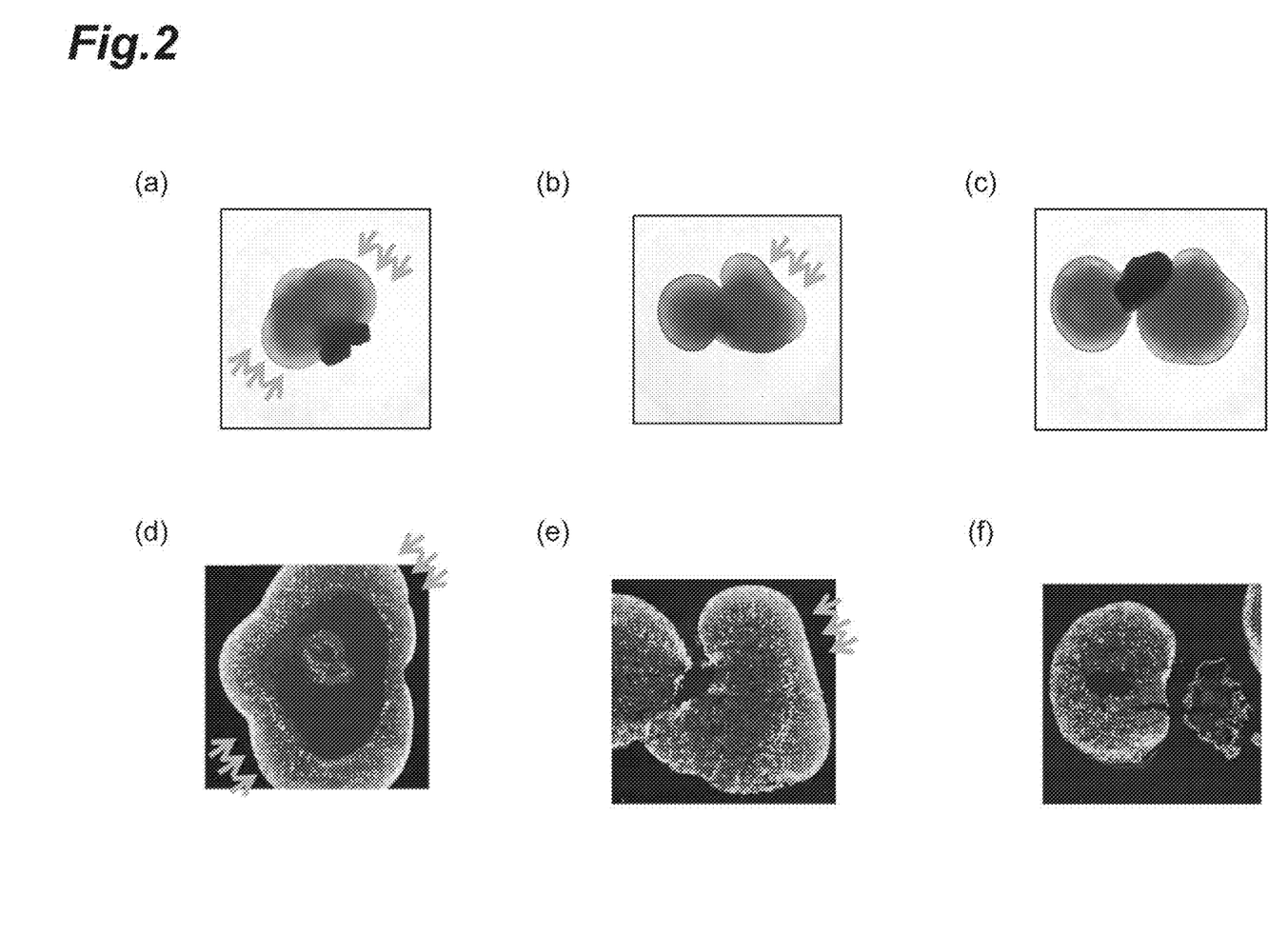
FIG. 2 shows images (bright-field images) of a cell aggregate and immunostaining images of a frozen section of the cell aggregate.

When a bright-field image (phase contrast image) of the cell aggregate from 63 days after the suspension culture started obtained in this manner was observed using an inverted microscope (ECLIPSE Ti commercially available from Nikon Corporation), the cell aggregate included a three-dimensional tissue and a part thereof included a continuous epithelial structure. Four of the above cell aggregate s were put into a 96-well dish, and bright-field color images (phase contrast images) were captured using an inverted microscope (ECLIPSE Ti commercially available from Nikon Corporation) with an objective lens (4×) and a color CCD camera (DS-Ri2) (FIGS. 2(a) to 2(c)).

The cell aggregate from 63 days after the suspension culture started was fixed using 4% paraformaldehyde to prepare frozen sections. Immunostaining of these frozen sections was performed using Rx (anti-Rax antibody, commercially available from Takara, guinea pig) which is one of retinal tissue markers, Chx10 (anti-Chx10 antibody, commercially available from Exalpha, sheep) which is one of retinal tissue markers, Ki67 (anti-Ki67 antibody, commercially available from Leica, rabbit) which is one of proliferating cell markers, or Crx (anti-Crx antibody, commercially available from Takara, rabbit). Immunostaining images of these immunostained sections were acquired using a confocal laser type microscope (commercially available from Olympus) (FIGS. 2(d) to 2(f)). The acquired immunostaining images were analyzed. The result was that it was found that epithelial tissue (in particular, neuroepithelial tissue) was formed on the outer circumference of the aggregate, and a continuous epithelial structure was formed in a part thereof (arrow parts in FIGS. 2(d) and 2(e)).

An immunohistochemical staining image and a bright-field image of the same cell aggregate were compared, and features in the continuous epithelial structure (arrow parts in FIGS. 2(a) and 2(b)) in the bright-field image corresponding to the continuous epithelial structure (arrow parts in FIGS. 2(d) and 2(e)) detected through immunohistochemical staining analysis were examined. The result was that, it was found that the continuous epithelial structure of retinal tissue included in the cell aggregate had morphologically the following Features 1 to 3 in the bright-field image.

Feature 1. A part (surface layer) close to the outer circumference of the cell aggregate has a high luminance value (is bright), and an inside part (a deep layer in the cells) with a certain depth from a surface layer of the cell aggregate has a small luminance value (is dark)

Feature 2. The outline of the cell aggregate is smooth (that is, an amount of variation in curvature is low).

Feature 3. The morphological features of Feature 1 and Feature 2 are continuous in the tangential direction of aggregates.

Here, the above-described conditions 1 to 4 were obtained based on the findings of the above features 1 to 3.

Figure 3:
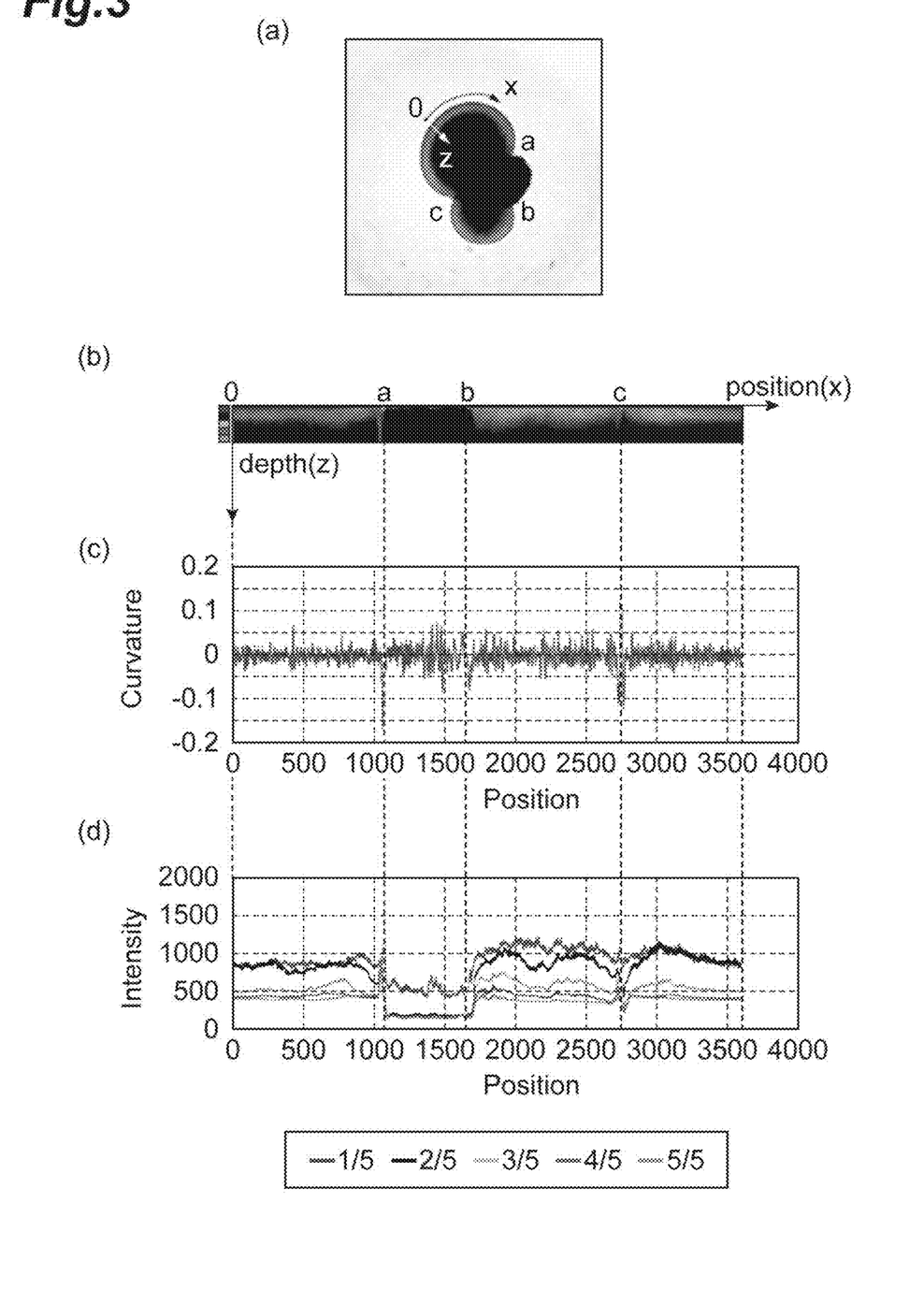
FIG. 3 shows an image (bright-field image) of a cell aggregate and processing results according to Example 1.

When the cell aggregate from 62 days after the suspension culture started prepared by the above method was visually observed using a phase contrast microscope (ECLIPSE Ti commercially available from Nikon Corporation), the cell aggregate included a three-dimensional tissue and a part thereof included a continuous epithelial structure. The cell aggregate was put into a 96-well dish, and a bright-field color image (phase contrast image) was captured using an inverted microscope (ECLIPSE Ti commercially available from Nikon Corporation) with an objective lens (4×) and a color CCD camera (DS-Ri2) (FIG. 3(a)). It was examined whether there was a region having the above morphological features of a, continuous epithelial structure in the image of the cell aggregate included in the bright-field image, and then it was confirmed that the cell aggregate included a continuous epithelial structure (FIG. 3(a)).

According to the method of the present embodiment, a region of a continuous epithelial structure was detected in the bright-field image. Here, in order to detect the outline, binarization processing, smoothing processing, and outline tracking processing were performed. In addition, in order to detect the region, the above conditions 1 to 4 were used for detection. FIGS. 3(b) to 3(d) show information acquired from the image in FIG. 3(a). In the present example, as described above, a region between 0 and a, a region between b and c, and a region between c and 0 in the image in FIG. 3(a) were determined as regions including a continuous epithelial structure. In addition, a region between a and b was determined as a region including no continuous epithelial structure.

As above, the image (bright-field image) of the cell aggregate was acquired, it was possible to acquire outline information based on the image, and it was possible to extract values indicating morphological characteristics of the cell aggregate from the image from the bright-field image and the outline information according to a curvature calculation operation and a luminance value depth distribution calculation operation. Then, it was found that, according to the obtained morphological characteristics (a curvature plot and a luminance value depth distribution plot), it was possible to detect and identify a region of a continuous epithelial structure according to conditions 1 to 4. Here, in the present example, after binarization processing, when expansion and reduction processing as smoothing processing was not performed and outline tracking processing was performed, it was not possible to calculate outline information in some images. Also in these cases, since it was possible to calculate outline information by performing smoothing processing, it was found that outline tracking processing could be performed in combination with smoothing processing.

Example 2

Bright-field color images (phase contrast images) of three different cell aggregates from 62 days after the suspension culture started prepared by the method described in Example 1 were captured by the method described in Example 1 (FIG. 4 to FIG. 6(a)). When determination was visually performed on the bright-field image by the method described in Example 1, it was confirmed that the cell aggregate of the image in FIG. 4 included a continuous epithelial structure. On the other hand, it was found that the cell aggregates in FIG. 5 and FIG. 6 did not include a continuous epithelial structure.

According to the method (the same method as in Example 1) of the present embodiment, a region of a continuous epithelial structure was detected in the bright-field images. Here, FIG. 4 to FIG. 6(b) to (d) show information acquired from the images in FIG. 4 to FIG. 6(a).

Figure 4:
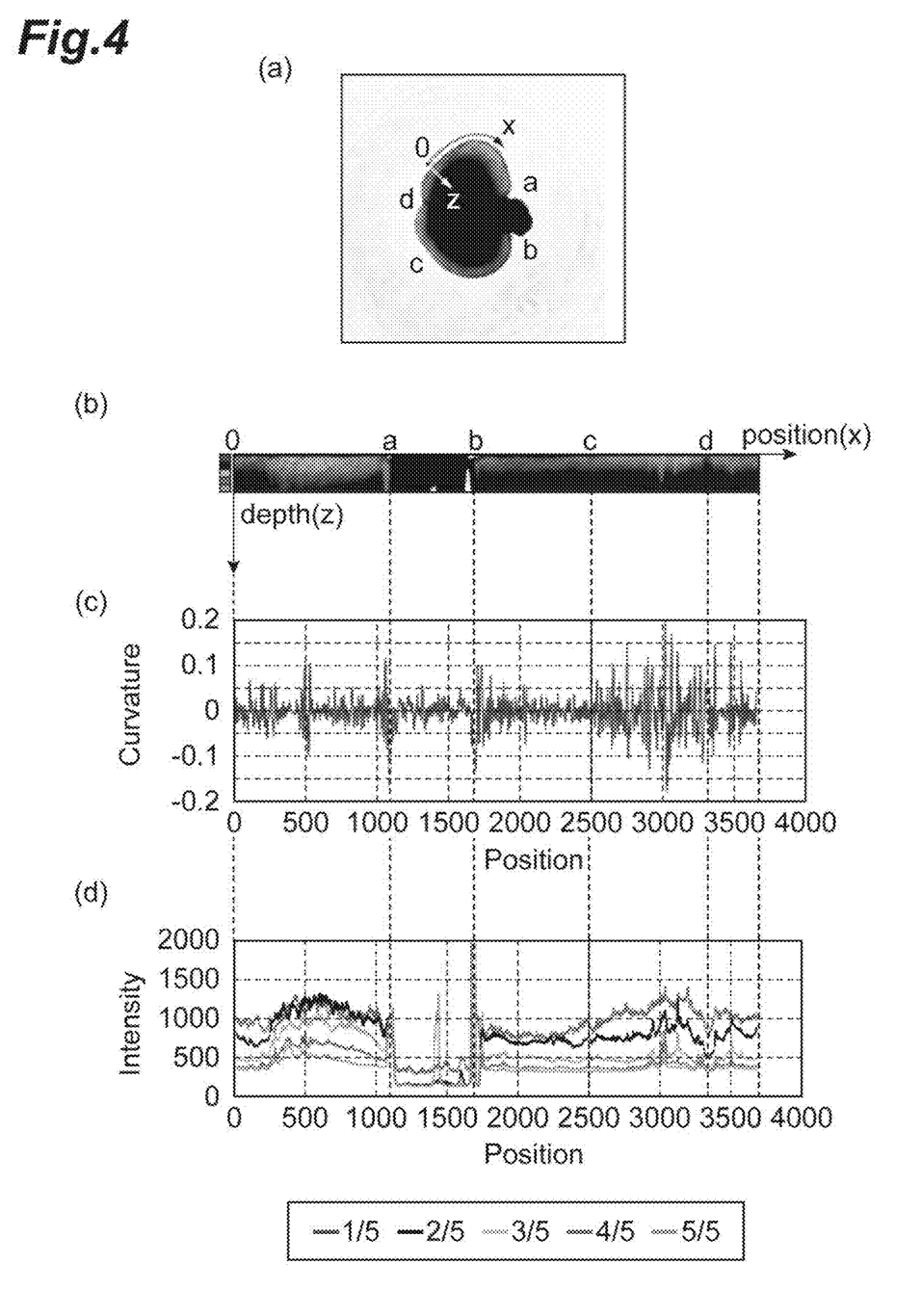
FIG. 4 shows an image (bright-field image) of a cell aggregate and processing results according to Example 2.
Figure 5:
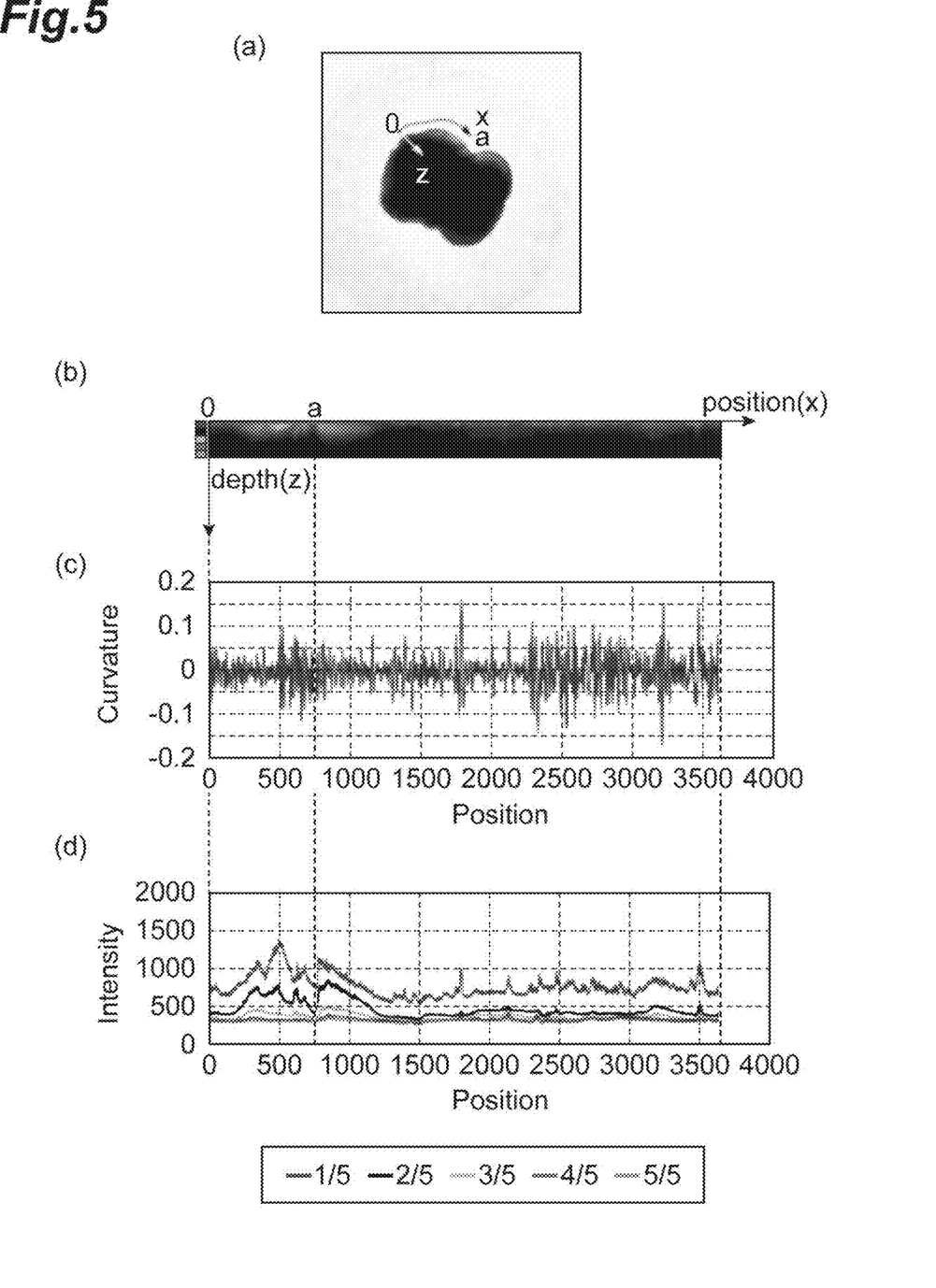
FIG. 5 shows an image (bright-field image) of a cell aggregate and processing results according to Example 2.
Figure 6:
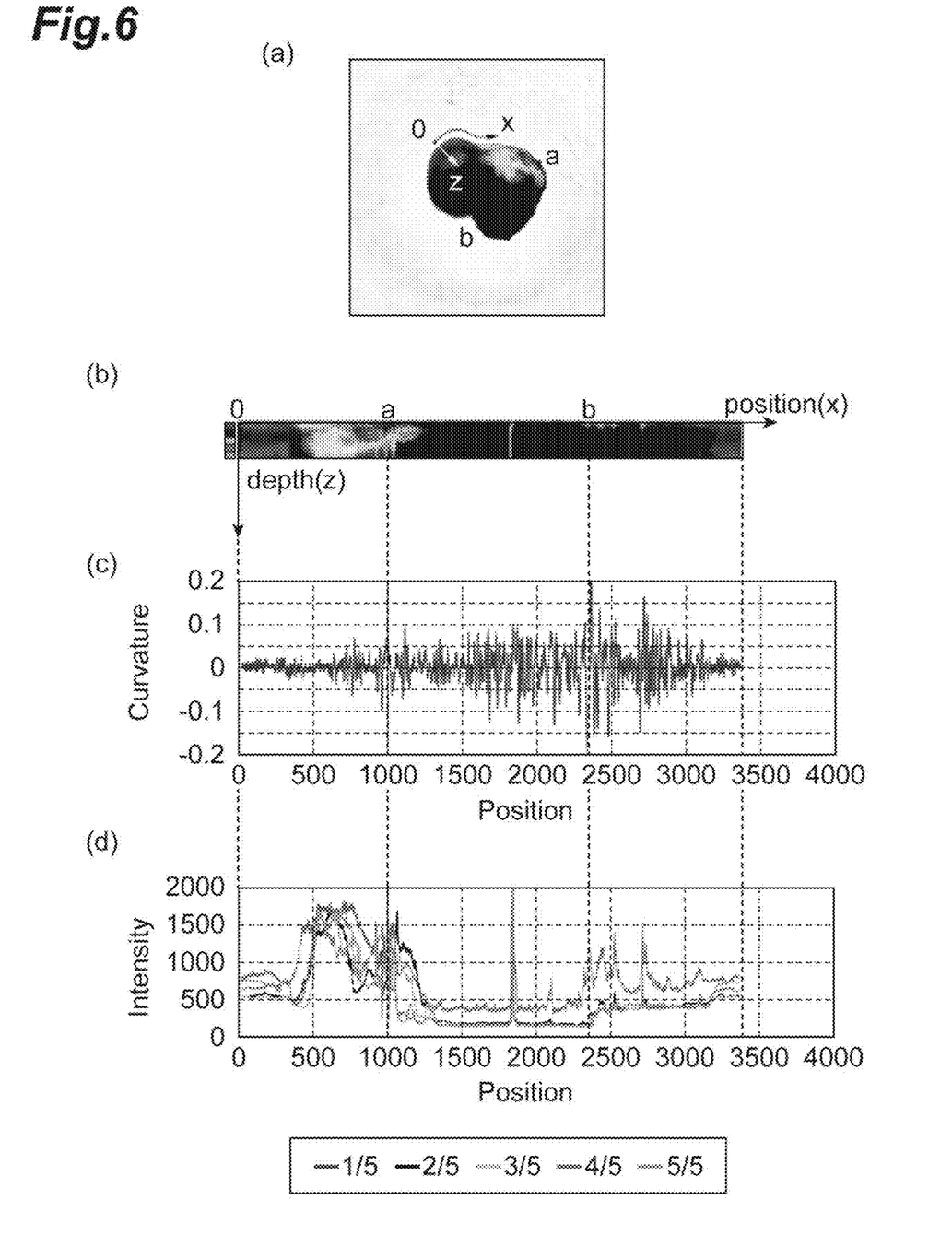
FIG. 6 shows an image (bright-field image) of a cell aggregate and processing results according to Example 2.

In the cell aggregate in FIG. 4, a region between 0 and a and a region between b and c in the image in FIG. 4(a) were determined as regions including a continuous epithelial structure. In addition, a region between a and b and a region between c and 0 were determined as regions including no continuous epithelial structure. In the cell aggregates in FIG. 5 and FIG. 6, all of the regions were determined as regions including no continuous epithelial structure.

That is, it was examined whether it is possible to detect a continuous epithelial structure from various for ins of cell aggregates. As a result, when the method of the present embodiment was used, a bright-field image was acquired as an image and it was possible to acquire outline information based on the image. In addition, it was possible to extract morphological characteristics of the image from the bright-field image and outline information according to a curvature calculation operation and a luminance value depth distribution calculation operation. Then, it was verified that, according to the obtained morphological characteristics (a curvature plot and a luminance value depth distribution plot), it was possible to detect and identify a continuous epithelial structure according to conditions 1 to 4.

Example 3

Figure 7:
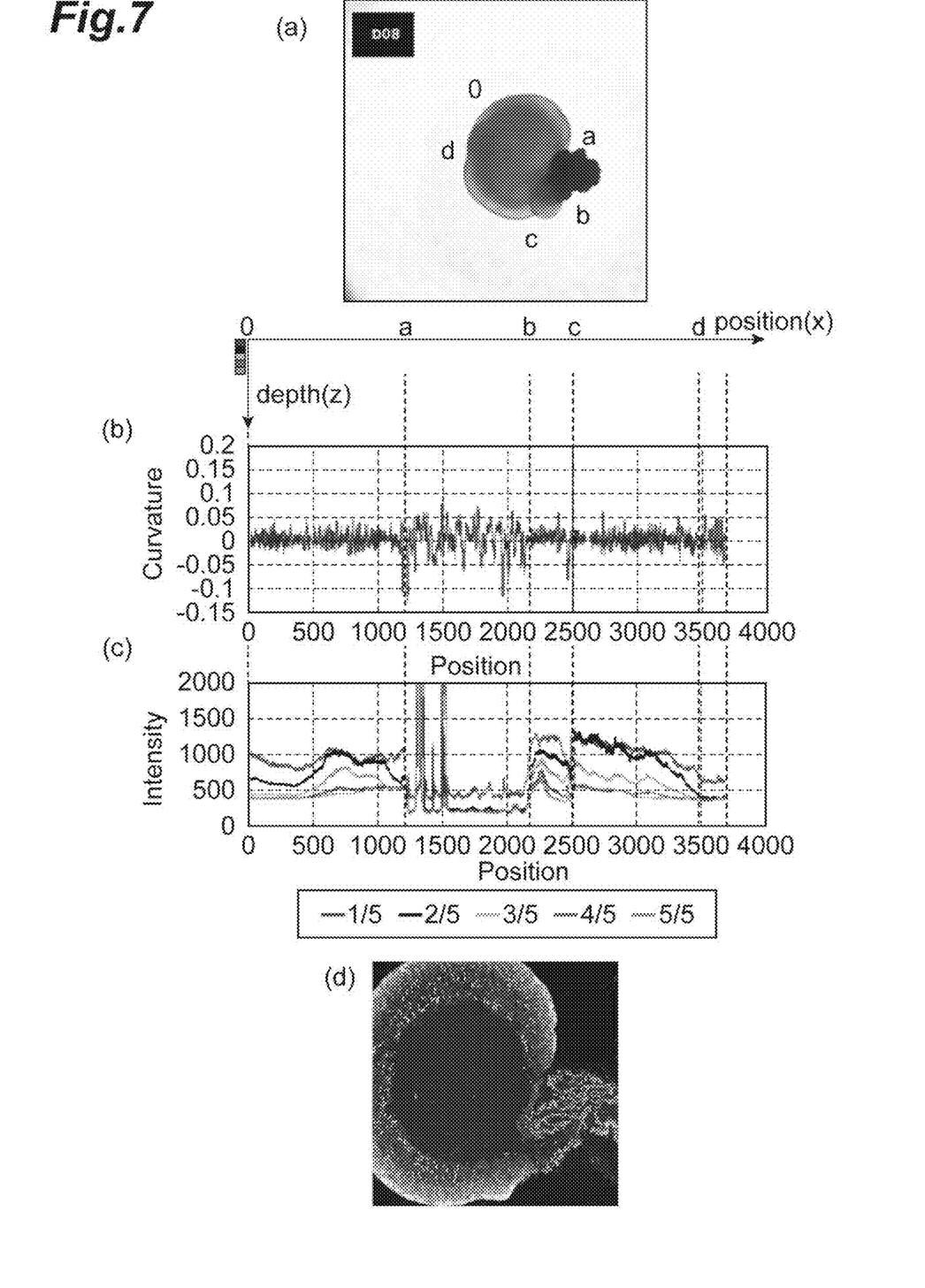
FIG. 7 shows an image (bright-field image) of a cell aggregate, processing results, and an immunostaining image of a frozen section of the cell aggregate according to Example 3.
Figure 8:
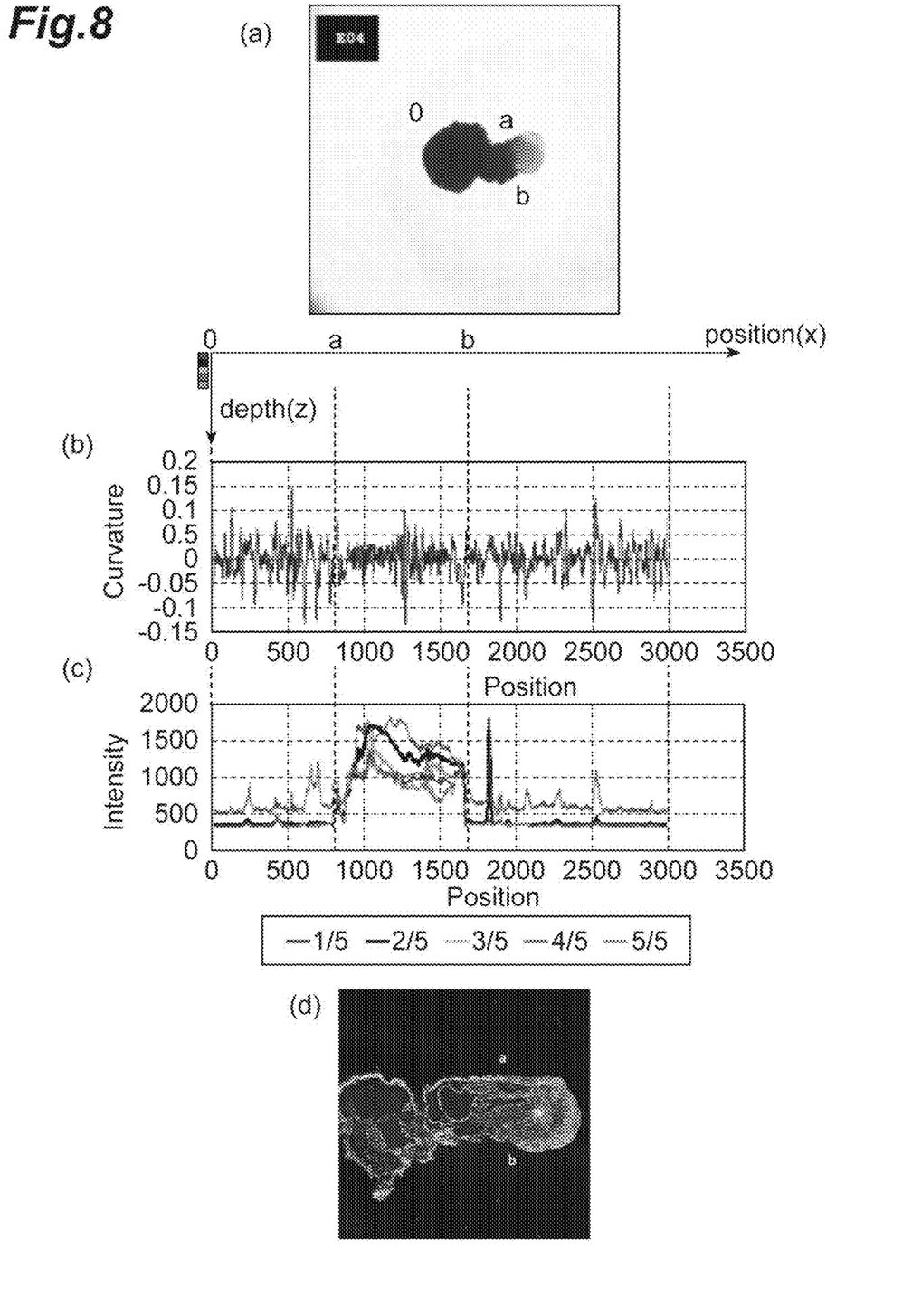
FIG. 8 shows an image (bright-field image) of a cell aggregate, processing results, and an immunostaining image of a frozen section of the cell aggregate according to Example 3.

Bright-field color images (phase contrast images) of two different cell aggregates from 63 days after the suspension culture started prepared by the method described in Example 1 were captured by the method described in Example 1 (FIG. 7 and FIG. 8(a)).

According to the method (the same method as in Example 1) of the present embodiment, a region of a continuous epithelial structure was detected in the bright-field images. Here, FIG. 7, and FIGS. 8(b) and (c) show information acquired from the images in FIG. 7 and FIG. 8(a).

In the cell aggregate in FIG. 7, a region between 0 and a, and a region between c and d in the image in FIG. 7(a) were determined as regions including a continuous epithelial structure. In addition, a region between a and b, a region between b and c, and a region between d and 0 were determined as regions including no continuous epithelial structure. In the cell aggregate in FIG. 8, all of the regions were determined as regions including no continuous epithelial structure.

It was examined whether the region (morphological characteristic) detected in the bright-field image of the cell aggregate according to the present embodiment was correlated with characteristics of an actual cell aggregate. The cell aggregates shown in FIG. 7 and FIG. 8(a) were fixed using 4% paraformaldehyde to prepare frozen sections. Immunostaining of these frozen sections was performed using Rx (anti-Rax antibody, commercially available from Takara, guinea pig) which is one of retinal tissue markers, Chx10 (anti-Chx10 antibody, commercially available from Exalpha, sheep) which is one of retinal tissue markers, Ki67 (anti-Ki67 antibody, commercially available from Leica, rabbit) which is one of proliferating cell markers, or Crx (anti-Crx antibody, commercially available from Takara, rabbit). Immunostaining images were acquired from these immunostained sections using a confocal laser type microscope (commercially available from Olympus) (FIG. 7 and FIG. 8(d)).

In the cell aggregate in FIG. 7, the obtained immunostaining images were analyzed and as the result, it was found that a region between 0 and a and a region between c and d were a continuous epithelial structure of the retinal tissue, and a region between a and b, region between b and c, and a region between d and 0 were not a continuous epithelial structure of the retinal tissue. Similarly, in the cell aggregate in FIG. 8, the obtained immunostaining image was analyzed and as a result, it was found that almost no continuous epithelial structure was included.

Based on such results, it was verified that, when the bright-field image of the cell aggregate was acquired and the bright-field image was image-analyzed according to the present embodiment, it was possible to detect morphological characteristics of the cell aggregate, and particularly, a continuous epithelial structure.

All cited patents, patent applications and documents mentioned in this specification are incorporated herein by reference in their entirety.

INDUSTRIAL APPLICABILITY

An embodiment of the present invention is useful in selecting types of useful cells in at least one of the medical and industrial fields. For example, when retinal tissue including a continuous epithelial structure can be selected from the cell aggregate including retinal tissue prepared from human iPS cells, it is possible to select high quality retinal tissue in at least one of the medical and industrial fields. At least one type of cell and tissue selected in an embodiment of the present invention is very beneficial as at least of a cellular medicine and a material used for screening for the efficacy and safety of compounds.

REFERENCE SIGNS LIST

10 Region detecting device
11 Input unit
12 Outline detection unit
13 Region detection unit
14 Output unit
20 Microscope

The invention claimed is:

1. A region detecting method which is a method of operating a region detecting device, the method comprising:
 an input step of inputting an image obtained by imaging a cell aggregate;
 an outline detecting step of detecting an outline of the cell aggregate together with an order along the outline in the image input in the input step;
 a region detecting step of detecting a region of a continuous epithelial structure included in the cell aggregate based on (1) the outline and order detected in the outline detecting step, and (2) luminance values of pixels in a direction from the outline to the cell aggregate in the image; and
 an output step of outputting information indicating the region detected in the region detecting step.

2. The region detecting method according to claim 1, wherein, in the outline detecting step, outline tracking processing is performed on the image, thereby detecting the outline of the cell aggregate.

3. The region detecting method according to claim 2, wherein, in the outline detecting step, smoothing processing is performed on the image before the outline tracking processing.

4. The region detecting method according to claim 1, wherein, in the region detecting step, the specific region is detected based on a shape of the outline in the image.

5. The region detecting method according to claim 4, wherein, in the region detecting step, a shape of the outline in the image is expressed as a curvature of each pixel constituting the outline in an outline tangential direction and the specific region is detected based on the curvature.

6. The region detecting method according to claim 1, wherein the cell aggregate includes retinal tissue.

7. A region detecting device comprising circuitry configured to:
 input an image obtained by imaging a cell aggregate;
 detect an outline of the cell aggregate together with an order along the outline in the image input;
 detect a region of a continuous epithelial structure included in the cell aggregate based on (1) the outline and order detected, and (2) luminance values of pixels in a direction from the outline of the cell aggregate in the image; and
 output information indicating the region detected.

* * * * *